US011524295B2

(12) United States Patent
Tonomura et al.

(10) Patent No.: US 11,524,295 B2
(45) Date of Patent: Dec. 13, 2022

(54) CHANNEL DEVICE AND METHOD FOR CONCENTRATING FINE PARTICLES (71) Applicant: Aipore Inc., Tokyo (JP)

(72) Inventors: Wataru Tonomura, Osaka (JP); Makusu Tsutsui, Osaka (JP); Kazumichi Yokota, Osaka (JP); Akihide Arima, Osaka (JP); Masateru Taniguchi, Osaka (JP); Tomoji Kawai, Osaka (JP)

(73) Assignee: AIPORE INC., Tokyo (JP)

( * ) Notice: Subject to any disclaimer, the term of this patent is extended or adjusted under 35 U.S.C. 154(b) by 516 days.

(21) Appl. No.: 16/614,707

(22) PCT Filed: May 9, 2018

(86) PCT No.: PCT/JP2018/017992
§ 371 (c)(1),
(2) Date: Nov. 18, 2019

(87) PCT Pub. No.: WO2018/212043
PCT Pub. Date: Nov. 22, 2018

(65) Prior Publication Data
US 2020/0070169 A1  Mar. 5, 2020

(30) Foreign Application Priority Data

May 19, 2017 (JP) .............................. JP2017-100218

(51) Int. Cl.
*B01L 3/00* (2006.01)
*B01D 29/44* (2006.01)
(Continued)

(52) U.S. Cl.
CPC ........ *B01L 3/502761* (2013.01); *B01D 29/44* (2013.01); *C12N 1/20* (2013.01);
(Continued)

(58) Field of Classification Search
CPC .............. B01D 2201/202; B01D 29/44; B01L 2200/0668; B01L 2300/0681;
(Continued)

(56) References Cited

U.S. PATENT DOCUMENTS 4,800,022 A    1/1989  Leonard
2006/0035386 A1  2/2006  Hattori et al.
(Continued)

FOREIGN PATENT DOCUMENTS

JP    S 62-502174 A    8/1987
JP    2004/354364      12/2004
(Continued)

OTHER PUBLICATIONS

JP Office Action in Application 2019-519195 dated Dec. 28, 2020, and English language machine translation thereof.
(Continued)

*Primary Examiner* — Jennifer Wecker
*Assistant Examiner* — Kathryn Elizabeth Limbaugh
(74) *Attorney, Agent, or Firm* — Kristina Castellano; Castellano PLLC (57) ABSTRACT Provided is a channel device that is capable of increasing the concentration of fine particles in a liquid only by use of fluid-dynamic flows without relying on electrostatic interactions. A channel device (1) in accordance with an embodiment of the present invention includes: a main channel (11) configured to allow a liquid containing fine particles to flow therethrough; a chamber (15) that is provided at an end of the main channel (11) and that is configured to store target fine particles which have increased in concentration; and a side channel (12) that is connected to a side face of the main channel (11) and that is configured to allow unwanted liquid
(Continued)

to drain therethrough, wherein at least one of a height and a width of the side channel (12) is smaller than a particle size of the fine particles.

6 Claims, 6 Drawing Sheets

(51) Int. Cl.
*C12N 1/20* (2006.01)
*G01N 1/40* (2006.01)

(52) U.S. Cl.
CPC ......... *G01N 1/40* (2013.01); *B01D 2201/202* (2013.01); *B01L 2200/0668* (2013.01); *B01L 2300/14* (2013.01)

(58) Field of Classification Search
CPC ........... B01L 2300/14; B01L 2300/161; B01L 2400/0688; B01L 2400/086; B01L 3/502707; B01L 3/502753; B01L 3/502761; C12N 1/20; C12Q 1/04; G01N 1/40
See application file for complete search history.

(56) References Cited

U.S. PATENT DOCUMENTS

| | | |
|---|---|---|
| 2006/0070951 A1 | 4/2006 | Baba et al. |
| 2011/0105982 A1 | 5/2011 | Leonard |
| 2014/0004501 A1 | 1/2014 | Talebpour et al. |
| 2015/0202549 A1 | 7/2015 | Gifford et al. |
| 2017/0175931 A1 | 6/2017 | Ichiki et al. |
| 2018/0093023 A1 | 4/2018 | Gifford et al. |

FOREIGN PATENT DOCUMENTS

| | | |
|---|---|---|
| JP | 2007-21465 | 2/2007 |
| JP | 2007-108087 | 4/2007 |
| JP | 2007/175684 | 7/2007 |
| JP | 2010-071857 A | 4/2010 |
| JP | 2011-514182 A | 5/2011 |
| JP | 2012-223683 | 11/2012 |
| JP | 2012-239991 | 12/2012 |
| JP | 2014-521322 | 8/2014 |
| JP | 2014-233209 | 12/2014 |
| JP | 5870323 | 2/2016 |
| JP | 2017-510450 | 4/2017 |
| WO | 2004/050220 A1 | 6/2004 |
| WO | 2016/006615 | 1/2016 |

OTHER PUBLICATIONS

English Translation of International Preliminary Report on Patentability for PCT/JP2018/017992, dated Nov. 21, 2019.
International Search Report for PCT/JP2018/017992 dated Aug. 7, 2018.
Wataru Tonomura et al., "Method of increasing microparticle concentration . . . ",The Instituted of Scientific and Industrial Research, Osaka University, May 23, 2017) , 35th CHEMINAS.
Wataru Tonomura et al., "Dual-Height Fluidic Channels . . . ",The Instituted of Scientific and Industrial Research, Osaka University, (Sep. 5, 2017) , Mechanical Engineering Congress, 2017 Japan.
"Dual-Height Fluidic-Channel-Integrated Micropore Senso . . . "(Oct. 24, 2017) The 21st International Conference on Miniaturized Systems for Chemistry and Life Sciences.
Yamada and Seki, "Hydrodynamic filtration for on-chip particle concentration and classification utilizing microfluidics", Lab on a Chip, 2005, 5, pp. 1233-1239.
TW Office Action in Application 107116514, dated Apr. 9, 2019 and translation.
Blanca H. Lapizco-Encinas et al. (2004) Anal. Chem., vol. 76 (Issue 6), pp. 1571-1579.
L. D'Amico et al. (2017) Lab on a Chip, vol. 17 (Issue 7), pp. 1340-1348.

CHANNEL DEVICE AND METHOD FOR CONCENTRATING FINE PARTICLES

CROSS REFERENCE TO RELATED APPLICATIONS

This application is a U.S. National Stage application of PCT/JP2018/017992 filed on May 9, 2018, which claims priority to Japanese patent application 2017-100218 filed on May 19, 2017, the contents of both of which are incorporated herein by reference.

TECHNICAL FIELD

The present invention relates to a channel device and a method of increasing the concentration of fine particles.

BACKGROUND ART

An attention has been attracted to methods of increasing the concentration of fine particles using a channel device which has a microchannel as a main structure. Such a method is carried out as a pretreatment for highly sensitive detection of fine particles that are contained in a liquid at low concentration. Among such methods, particularly a dielectrophoresis method, which uses a combination of a microchannel and microelectrodes, is a typical technique to control fine particles in a liquid.

For example, Non-patent Literature 1 reports that bacteria were separated from whole blood by a dielectrophoresis method. Similarly, Non-patent Literature 2 reports that live bacteria and dead bacteria were separated from each other by a dielectrophoresis method. These dielectrophoresis methods are based on the principle that fine particles are captured at and released from the outer periphery of a microelectrode at which electric field strength is maximum.

Also known is a technique to distribute fine particles, which are flowing through a channel in a channel device, into different channels by their size. Such a technique is disclosed in, for example, Patent Literatures 1 to 3.

CITATION LIST

Patent Literatures

[Patent Literature 1]
Specification of Japanese Patent No. 5870323 (Publication date: Feb. 24, 2016)
[Patent Literature 2]
Japanese Patent Application Publication Tokukai No. 2004-354364 (Publication date: Dec. 16, 2004)
[Patent Literature 3]
Japanese Patent Application Publication Tokukai No. 2012-223683 (Publication date: Nov. 15, 2012)

Non-Patent Literatures

[Non-patent Literature 1]
L. D'Amico et al. (2017) Lab on a Chip, Vol. 17 (Issue 7), pp. 1340-1348
[Non-patent Literature 2]
Blanca H. Lapizco-Encinas et al. (2004) Anal. Chem., Vol. 76 (Issue 6), pp. 1571-1579

SUMMARY OF INVENTION

Technical Problem

However, methods of increasing the concentration of fine particle using electrostatic interactions, like a dielectrophoresis method, may result in adsorption of fine particles on the electrode surface. Furthermore, according to the above methods, the spatial range of effective electric fields is limited. In addition, the above methods necessitate setting electrophoresis parameters according to the properties of fine particles and/or the difference in dielectric constant between the fine particles and a liquid.

An aspect of the present invention was made in view of the above conventional issues, and an object thereof is to provide a channel device and a method of increasing the concentration of fine particles each of which is capable of increasing the concentration of fine particles in a liquid without relying on electrostatic interactions.

Solution to Problem

The inventors of the present invention have studied hard in order to attain the above object, and found that a channel device which has a specific channel structure makes it possible to capture fine particles and increase the concentration of fine particles only using fluid-dynamic flows without relying on electrostatic interactions. On the basis of this finding, the inventors accomplished the present invention. Specifically, the present invention encompasses the following features.

<1> A channel device including: a main channel configured to allow a liquid containing fine particles to flow therethrough; a chamber that is provided at an end of the main channel and that is configured to store target fine particles which have increased in concentration; and a side channel that is connected to a side face of the main channel and that is configured to allow unwanted liquid to drain therethrough, in which at least one of a height and a width of the side channel is smaller than a particle size of the target fine particles.

<2> The channel device described in <1>, in which: the side channel has opposite first and second ends, the first end being connected to the main channel; and the side channel has the second end connected to a liquid drainage channel, the liquid drainage channel having a width that is equal to or greater than the width of the side channel and having a height that is equal to or greater than the height of the side channel.

<3> The channel device described in <1> or <2>, in which a liquid flow preventer part is provided between the main channel and the chamber.

<4> The channel device described in any one of <1> to <3>, including a plurality of the side channels.

<5> A method of increasing a concentration of target fine particles, the method including: an introducing step including introducing a liquid containing fine particles into a main channel; a capturing step including allowing the liquid to drain into a side channel connected to a side face of the main channel and capturing target fine particles at a place where the side channel and the main channel are connected together; a releasing step including releasing, into the main channel, the target fine particles thus captured; and a concentrating step including allowing the target fine particles thus released to move into a chamber provided at an end of the main channel so that the target fine particles which have increased in concentration are stored in the chamber, in which at least one of a height and a width of the side channel is smaller than a particle size of the target fine particles.

<6> The method described in <5>, in which: the side channel has opposite first and second ends, the first end being connected to the main channel; and the side channel has the second end connected to a liquid drainage channel, the liquid drainage channel having a width that is equal to or greater than the width of the side channel and having a height that is equal to or greater than the height of the side channel.

<7> The method described in <5> or <6>, in which a liquid flow preventer part is provided between the main channel and the chamber.

<8> The method described in any one <5> to <7>, in which a plurality of the side channels are provided.

Advantageous Effects of Invention

An aspect of the present invention brings about an effect of making it possible to provide a channel device and a method of increasing the concentration of fine particles each of which is capable of increasing the concentration of fine particles in a liquid without relying on electrostatic interactions.

DESCRIPTION OF EMBODIMENTS

The following description will discuss example embodiments of the present invention in detail. Note, however, that the present invention is not limited to such embodiments. In this specification, the numerical ranges "A to B" mean "not less than A and not more than B", unless otherwise noted. Also note that, for convenience of description, members having identical functions are assigned identical referential numerals, and their descriptions are not repeated.

[1. Channel Device]

A channel device in accordance with an embodiment of the present invention includes: a main channel configured to allow a liquid containing fine particles to flow therethrough; a chamber that is provided at an end of the main channel and that is configured to store target fine particles which have increased in concentration; and a side channel that is connected to a side face of the main channel and that is configured to allow unwanted liquid to drain therethrough, wherein at least one of the height and width of the side channel is smaller than the particle size of the target fine particles.

According to the above channel device, target fine particles which are carried by a flow toward the side channel can be captured at the entrance to the side channel. Furthermore, unwanted liquid is allowed to drain into the side channel, and therefore the target fine particles which have increased in concentration can be stored in the chamber that is connected to the main channel. Accordingly, the channel device is capable of increasing the concentration of the target fine particles in a liquid without relying on electrostatic interactions.

The channel device in accordance with an embodiment of the present invention is different from the techniques disclosed in Patent Literatures 1 to 3 in that the channel device in accordance with an embodiment of the present invention allows unwanted liquid to drain through the side channel and is thereby capable of increasing the concentration of target fine particles. The following description briefly discusses this aspect.

An automated cancer cell separator device disclosed in Patent Literature 1 is to introduce cancer cells and the other cells into respective different channels, by providing a part in which channel height is less than the average diameter of the cancer cells. A fine particle controlling unit disclosed in Patent Literature 2 is to control the direction of flow of fine particles which are flowing through a channel, by providing, for example, a region that does not allow passage of fine particles of a certain size or greater. A fine particle separating device disclosed in Patent Literature 3 is to introduce, into different outlets, fine particles that can pass through a filter and fine particles that cannot pass through the filter.

The devices disclosed in the above literatures introduce fine particles, separated by their size, into different channels; however, the devices do not have the function of separating unwanted liquid from the fine-particle-containing liquid and allowing the unwanted liquid to drain away (that is, the devices do not have the function of increasing the concentration of fine particles). On the contrary, the channel device in accordance with an embodiment of the present invention includes a side channel(s), which makes it possible to separate fine particles by their size and also possible to allow unwanted liquid to drain away and increase the concentration of fine particles.

As used herein, the term "unwanted liquid" refers to, for example, a dispersion medium in which fine particles are dispersed. In one embodiment, the "unwanted liquid" may contain fine particles that are not to be increased in concentration (i.e., fine particles that are smaller in particle size than fine particles that are to be increased in concentration). The channel device in accordance with an embodiment of the present invention allows unwanted liquid to drain through the side channel(s), and is capable of storing target fine particles increased in concentration in a chamber.

In this specification, the term "channel device" refers to a device including a channel structure which allows a liquid to flow therethrough. It is preferable that the liquid flows by capillary action.

Figure 1:
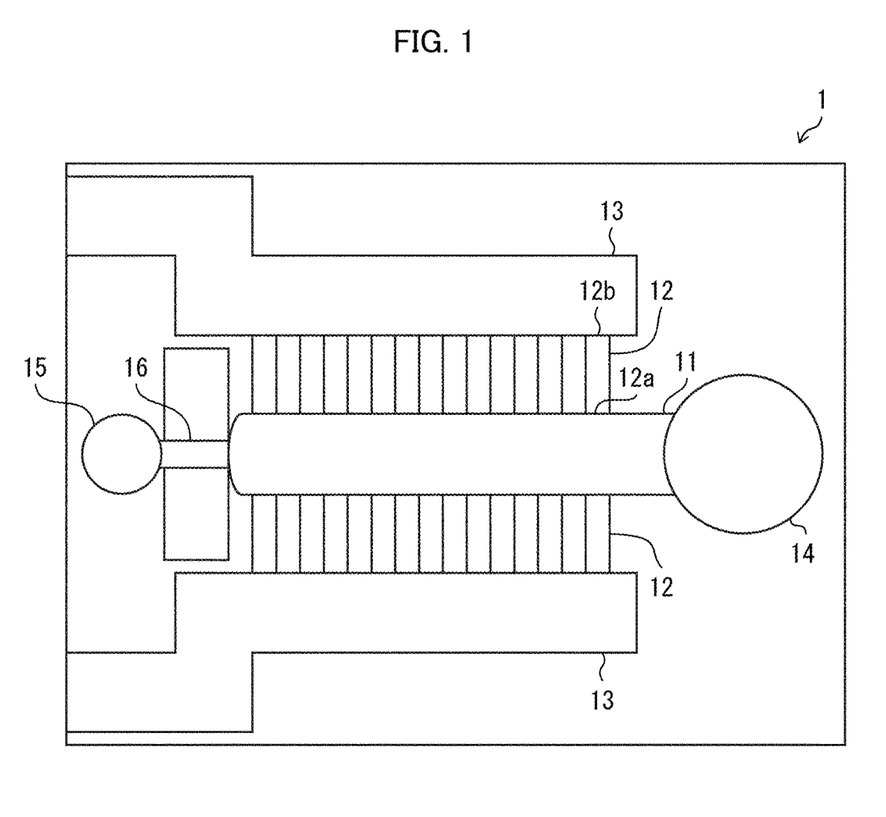
FIG. 1 schematically illustrates a structure of a channel device in accordance with an embodiment of the present invention.

The following description will discuss a structure of a channel device in accordance with an embodiment of the present invention with reference to FIG. 1. FIG. 1 schematically illustrates a structure of a channel device 1 in accordance with an embodiment of the present invention.

The channel device 1 includes a main channel 11, side channels 12, liquid drainage channels 13, a liquid inlet part 14, a chamber 15, and a liquid flow preventer part (water-repellent channel 16).

Note that, in this specification, the term "connected" as in, for example, "channels are connected together" means that the channels or the like are in communication with each other such that a liquid can flow between them.

<1-1. Main Channel>

The main channel 11 is a channel through which a fine-particle-containing liquid flows. The length, width, and height of the main channel 11 can be selected appropriately according to, for example, the particle size of fine particles which flow through the channel device 1, the amount of the liquid which flows through the channel device 1, and the number of the side channels 12 connected to the main channel 11. For example, the main channel 11 can have a length of 1 mm to 20 mm, a width of 100 µm to 500 µm, and a height of 10 µm to 200 µm. Note that, in this specification, the length of a main channel refers to a dimension of the main channel in a direction in which the liquid flows through the main channel.

The shape of the main channel 11 is not limited to a linear shape as illustrated in FIG. 1. The main channel 11 may be, for example, a meandered channel. For increasing the chances of contact between fine particles in the liquid and the side channels, the shape of the main channel 11 is preferably meandered. On the contrary, for making channel design easy, the shape of the main channel 11 is preferably linear. The shape of a cross section of the main channel 11 perpendicular to the direction of flow of the liquid is not particularly limited as well, and may be a quadrangular or circular shape.

The main channel 11 may have the liquid inlet part 14 at one end thereof. The liquid inlet part 14 is a part through which the fine-particle-containing liquid is introduced and thereby allowed to flow through the main channel 11. The liquid inlet part 14 may be a simple hole made in the one end of the main channel 11 or may be, for example, a reservoir as illustrated in FIG. 1. The capacity of the liquid inlet part 14 can be selected as appropriate according to, for example, the amount of the fine-particle-containing liquid to be introduced.

The main channel 11 of the channel device 1 preferably has a hydrophilic inner surface (i.e., surface which makes contact with the liquid). For example, the inner surface of the main channel 11 may have a silicon oxide ($SiO_x$) film formed thereon or may have functional groups thereon such as hydroxyl group, carbonyl group, aldehyde group, and/or carboxyl group. The inner surface of the main channel 11 may have been surface-treated by, for example, an oxygen plasma method, a vacuum ultraviolet exposure, or a fluorine gas treatment.

When the inner surface of the main channel 11 shows a hydrophilic property, the flow of the introduced liquid through the main channel 11, in a case where the liquid is an aqueous dispersion, is facilitated by the effect of capillary action. This shortens the time taken for the concentration of fine particles to be increased.

<1-2. Side Channel>

The main channel 11 has the side channels 12 connected to side faces thereof. Hereinafter, a place where the main channel 11 and a side channel 12 are connected together is referred to as "first junction 12a". That is, the first junction 12a can also be considered an entrance from the main channel 11 to the side channel 12. The side channels 12 are channels through which a liquid is guided from the main channel 11 to the outside of the main channel 11. The side channels 12 allow unwanted liquid to drain away. At least one of the height and width of each of the side channels 12 is smaller than the particle size of target fine particles 2. This makes it possible to capture target fine particles 2, which are carried by flows toward the side channels 12, at the first junctions 12a.

Figure 2:
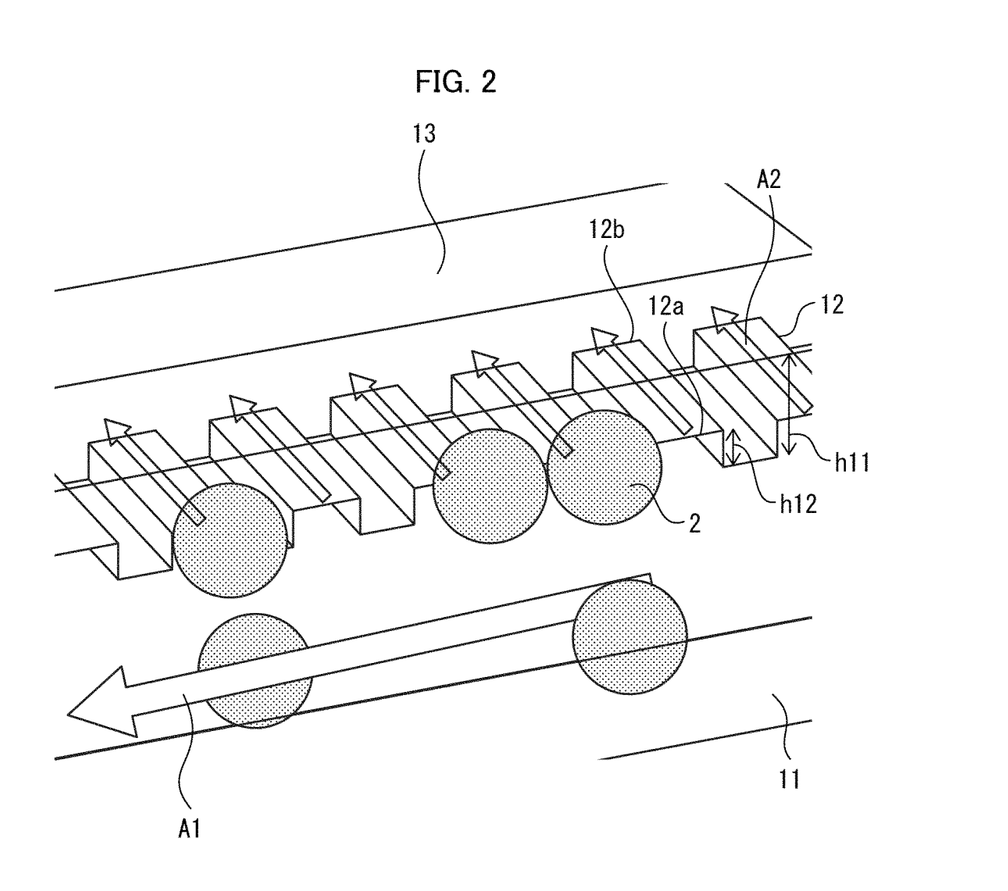
FIG. 2 schematically illustrates a structure of side channels and their surroundings of a channel device in accordance with an embodiment of the present invention.

FIG. 2 schematically illustrates a structure of the side channels 12 and their surroundings of the channel device 1 in accordance with an embodiment of the present invention. When a liquid passes through the channel device 1, the following kinds of flow occur: a flow of a liquid passing through the main channel 11 (such a flow is hereinafter referred to as "flow A1"); and a flow of a liquid passing through each side channel 12 (such a flow is hereinafter referred to as "flow A2"). The arrows indicated by A1 and A2 each represent the direction in which the liquid flows. When target fine particles 2 carried by the flow A1 approach the vicinities (first junctions 12a) of the side channels 12, the target fine particles 2 go into the flows A2 and change their travel direction toward the side channels 12. Note, however, that a height $h_{12}$ of each side channel 12 at the first junction 12a is smaller than the particle size of fine particles 2 that are to be increased in concentration (such fine particles may be referred to as "target fine particles"). With this structure, the target fine particles 2, which have a particle size greater than the height $h_{12}$ of the side channels 12, cannot pass through the first junctions 12a and therefore cannot enter the side channels 12. It follows that the target fine particles 2 stop moving (captured) at the first junctions 12a.

Then, the captured target fine particles 2 are released so that they go back into the flow A1, and thereby the target fine particles 2, which have increased in concentration, can be stored in the chamber 15 provided at the end of the main channel 11.

FIG. 2 illustrates an example in which the height of each side channel 12 is smaller than the particle size of the target fine particles 2. Note, however, that an arrangement in which the width of each side channel 12 is smaller than the particle size of the target fine particles 2 may be employed, as described earlier. Note that an arrangement in which the height of each side channel 12 is smaller than the particle size of the target fine particles 2 is more advantageous than an arrangement in which the width of each side channel 12 is smaller than the particle size of the target fine particles 2 in that the side channels 12 are easier to fabricate.

Note that the main channel 11 has a size that allows the fine particles 2 to flow therethrough. This means that, in FIG. 2, the height $h_{12}$ of each side channel 12 at the first junction 12a is less than a height $h_{11}$ of the main channel 11 at the first junction 12a. That is, there is a height difference between the main channel 11 and the side channels 12.

The length, width, and height of each side channel 12 and the number of side channels 12 can be selected appropriately according to the amount of a liquid that flows through the channel device 1, the number of fine particles contained in the liquid, and/or the like. Note that, in this specification, the term "length of a side channel" refers to a dimension of the side channel in a direction in which the liquid flows through the side channel. The width and height of each side channel 12 are preferably small to the extent that target fine particles to be captured do not aggregate. For example, it is preferable that one target fine particle is captured at one side channel 12. Furthermore, generally, when the length of each side channel 12 is shorter and the number of side channels 12 is greater, a liquid drains away more quickly; therefore, the length of each side channel 12 is preferably shorter and the number of side channels 12 is preferably greater.

For example, the length of each side channel 12 may be 1 µm to 100 µm or 1 µm to 50 µm. The width and/or height of the side channel 12 may be 0.05 µm to 10 µm, 0.05 µm to 5 µm, 0.05 µm to 0.5 µm, or 0.05 µm to 0.15 µm. The number of side channels 12 may be one or two or more. For example, the number of side channels 12 may be 1 to 1000, 100 to 800, or 300 to 700.

Note that the width and/or height of the side channel 12 needs to be smaller than the particle size of the target fine particles 2 only at the first junction 12a. That is, the width and/or height of the side channel 12 at places other than the first junction 12a may be equal to or greater than the particle size of the target fine particles 2.

Note, here, that the channel device 1 may include a plurality of side channels 12 having different heights. Such an arrangement makes it possible for a single channel device to capture target fine particles of different particle sizes. Alternatively, a plurality of channel devices 1 which are different in height of side channels 12 may be joined together. According to such an arrangement, the respective channel devices 1 are capable of isolating target fine particles of different particle sizes from a single liquid sample and increasing the concentration of the particles (for example, red blood cells, white blood cells, and blood platelets can be isolated from blood and increased in concentration).

Alternatively or additionally, the following arrangement may be employed: the channel device 1 is designed so that only some of the fine particles flowing through the main channel 11 can pass through the side channel(s) 12; and thereby the fine particles are separated by their particle size. According to such an arrangement, fine particles that cannot pass through the side channel(s) 12 remain inside the main channel 11, whereas particles that can pass through the side channel(s) 12 flow out of the main channel 11. As such, it is possible to isolate only target fine particles that cannot pass through the side channel(s) 12 and increase the concentration of those particles. The particles that can pass through the side channel(s) 12 can be recovered and increased in concentration by recovering the liquid that has flowed out through the side channel(s) 12 and subjecting it to another channel device 1 (in which at least one of the width and height at the first junction 12a is different from that of the previously used channel device 1).

The channel device 1 may be arranged such that a row of a plurality of side channels 12 is provided on a side face of the main channel 11 or may be arranged such that two or more such rows are provided on opposite side faces of the main channel 11. FIG. 1 illustrates an example arrangement in which two rows each consisting of a plurality of side channels 12 are provided.

Furthermore, similarly to the main channel 11, the inner surface of the side channel(s) 12 (i.e., surface which makes contact with a liquid) is preferably hydrophilic.

<1-3. Liquid Drainage Channel>

Each side channel 12 may have the other end, which is opposite from the end connected to the main channel 11 (i.e., opposite from the first junction 12a), connected to a liquid drainage channel 13. A place where the side channel and the liquid drainage channel 13 are connected together is hereinafter referred to as "second junction 12b". The liquid drainage channel 13 is a channel through which a liquid, which has flowed from the main channel 11 into the side channels 12, drains away.

The shape of the liquid drainage channel is not particularly limited. The liquid drainage channel 13 may be a reservoir which does not form any channel, provided that the liquid drainage channel 13 has the function of allowing a liquid, which has flowed from the main channel 11 into the side channels 12, to drain away. For enhancing the function of allowing a liquid to drain out of the main channel 11, the liquid drainage channel 13 may have a tube or the like connected thereto which allows a liquid to drain from the liquid drainage channel 13 to the outside of the range shown in FIG. 1.

The length, width, and height of the liquid drainage channel 13 can be selected appropriately according to, for example, the amount of a liquid that flows through the channel device 1. Note that, in this specification, the term "length of a liquid drainage channel" refers to a dimension of the liquid drainage channel in a direction in which a liquid flows through the liquid drainage channel. For example, the liquid drainage channel 13 can have a length of 1 mm to 20 mm, a width of 50 µm to 200 µm, and a height of 10 µm to 200 µm. The liquid drainage channel 13 is preferably wide and high enough to allow a liquid to drain away by pressure, and preferably has a width that is equal to or greater than the width of each side channel 12 and has a height that is equal to or greater than the height of the side channel 12. This arrangement allows fine particles that are smaller than fine particles to be increased in concentration (that is, particles having a size that can pass through the side channels 12) to be discharged through the liquid drainage channel. Note that the height of the liquid drainage channel 13 and the height of each side channel 12 here are intended to mean the heights at the second junction 12b.

A structure in which a plurality of side channels 12 are connected to a single liquid drainage channel 13 may be employed. For example, as illustrated in FIG. 1, the channel device 1 may include two or more of such structures.

Furthermore, similarly to the main channel 11, the inner surface of the liquid drainage channel 13 (i.e., surface which makes contact with a liquid) is preferably hydrophilic.

<1-4. Chamber>

The main channel 11 has, at the other end thereof, the chamber 15 for storing fine particles increased in concentration. The chamber 15 is located at the opposite end of the main channel 11 from the end (liquid inlet part 14) through which a liquid is introduced. That is, the chamber 15 is located downstream in the flow direction of the main channel 11. The chamber 15 serves to receive fine particles that are to be increased in concentration. The capacity of the chamber 15 can be selected as appropriate according to, for example, the particle size and/or the number of target fine particles to be captured.

Target fine particles 2, after released from the first junctions 12a, pass through the main channel 11 to reach the chamber 15. As described earlier, unwanted liquid drains into the side channels 12; therefore, in the chamber 15, the target fine particle concentration is greater than what it was when the target fine particles were introduced.

Furthermore, similarly to the main channel 11, the inner surface of the chamber 15 (i.e., surface which makes contact with a liquid) is preferably hydrophilic.

<1-5. Liquid Flow Preventer Part>

It is preferable that the main channel 11 and the chamber 15 are connected together with the liquid flow preventer part between them. The liquid flow preventer part is a member that has the function of temporarily preventing the flow of a liquid between the main channel 11 and the chamber 15. The liquid flow preventer part makes it possible to prevent a liquid from entering the chamber 15 while liquid drainage and capturing of target fine particles are being carried out.

For example, the liquid flow preventer part is the water-repellent channel 16. The inner surface of the water-repellent channel 16 is water-repellent, and therefore, in a case where a liquid introduced into the main channel 11 is an aqueous dispersion, the aqueous dispersion usually cannot pass through the water-repellent channel 16. The water-repellent channel 16 is preferably designed such that its inner surface (i.e., surface which makes contact with a liquid) is water-repellent and that a liquid can pass through the water-repellent channel 16 when a pressure difference is caused. For example, the inner surface of the water-repellent channel 16 may have a silicon carbide ($SiC_x$) film formed thereon, may have functional groups formed thereon such as methyl group, or may be formed from a fluorine compound (for example, trifluoromethyl group is introduced into the surface).

On the contrary, in a case where a liquid introduced into the main channel 11 is a nonpolar dispersion, the liquid flow preventer part can be a hydrophilic channel. Note that, in the case where a liquid introduced into the main channel 11 is a nonpolar dispersion, the inner surfaces (i.e., surfaces which make contact with the nonpolar dispersion) of the main channel 11, the side channels 12, the liquid drainage channel 13, and the chamber 15 are preferably hydrophobic, contrary to the foregoing descriptions. Such hydrophobic inner surfaces may be achieved by, for example, forming a silicon carbide ($SiC_x$) film, introducing functional groups such as methyl group, or forming the inner surfaces from a fluorine compound (for example, introducing trifluoromethyl group into the surfaces).

In another example, the liquid flow preventer part is a mechanism to temporarily block the main channel 11. Such a mechanism is, for example, a diaphragm microvalve that is driven by pneumatic pressure.

In order to send target fine particles to the chamber 15, it is only necessary to, for example, (i) cause a liquid pressure difference such that the pressure at the end of the main channel 11 at which a liquid is introduced (i.e., the pressure at the liquid inlet part 14-side end of the main channel 11) is higher or (ii) release the blockage of the main channel 11.

This makes it possible to easily control when the target fine particles are sent into the chamber 15. This makes it possible to, for example, in a case where a sensor is connected to the chamber 15, prevent the sensor from becoming dirty before measurement, and thus possible to achieve more accurate measurement of the concentration of fine particles.

<1-6. Other Configuration>

The channel device 1 may include a feature to cause a liquid pressure difference such that the pressure at the end of the main channel 11 at which a liquid is introduced is higher (i.e., a feature configured to generate a positive pressure). For example, a fluid pressure controller may be connected to the end of the main channel 11 at which a liquid is introduced (i.e., the liquid inlet part 14-side end of the main channel 11).

When a liquid pressure difference is caused across the main channel 11 such that the pressure at the end at which a liquid is introduced is higher, the following advantage is achieved. Specifically, assume that the liquid has drained into the side channels 12 and target fine particles are captured at the first junctions 12a. In this situation, when a positive pressure is applied and thereby an additional liquid is passed, the captured target fine particles 2 can be released and moved to the chamber 15. The application of a positive pressure also makes it possible to cause the target fine particles 2 to pass through the foregoing liquid flow preventer part (such as water-repellent channel 16) and send them to the chamber 15.

The channel device 1 may include a feature to cause a liquid pressure difference between the first junction 12a and the second junction 12b of each side channel 12. Such a feature can be, for example, a feature configured to cause a liquid pressure difference between the main channel 11 and the side channels 12. A more specific example is an arrangement in which a fluid pressure controller is connected to the main channel 11, the side channel(s) 12, and/or the liquid drainage channel(s) 13.

When a liquid pressure difference is caused between the first junction 12a and the second junction 12b of each side channel 12, the following advantage is achieved. In a case where a fluid pressure at the first junction 12a is higher than a fluid pressure at the second junction 12b (e.g., in a case where the pressure at the first junction 12a-side end of the side channel 12 is positive pressure or in a case where the pressure at the second junction 12b-side end of the side channel 12 is negative pressure), the flow rate of the liquid flowing through the side channel 12 toward the liquid drainage channel 13 increases, making it possible to shorten the time taken for the liquid to drain. On the contrary, in a case where the fluid pressure at the first junction 12a is lower than the fluid pressure at the second junction 12b, the liquid flows back from the liquid drainage channel 13 to the side channel 12, making it possible to release the target fine particle(s) captured at the first junction 12a into the main channel 11.

Furthermore, the channel device 1 may have any of various kinds of sensor connected thereto. Such a sensor can be connected to, for example, the chamber 15.

<1-7. Fine-Particle-Containing Liquid (Liquid Containing Fine Particles)>

A target to be concentrated is not particularly limited, provided that a fine-particle-containing liquid is concentrated. The particle size, concentration, and type of fine particles, type of dispersion medium, and the like are not particularly limited. In this specification, the fine-particle-containing liquid may also be referred to as a dispersion liquid. Note that the channel device only needs to be capable of increasing the concentration of fine particles of a desired type(s), and does not need to increase the concentrations of all types of fine particles contained in the liquid. For example, unnecessary fine particles may be discharged through a side channel(s) to a liquid drainage channel(s) or the like.

The particle size of fine particles is, for example, major diameter, minor diameter, Feret diameter, sphere equivalent diameter (Heywood diameter), effective diameter, or the like, each of which is determined by a known method of finding particle size. The method of finding the particle size of fine particles can be selected appropriately according to the properties of the fine particles. The particle size of fine particles may be, for example, not more than 100 μm.

The concentration of fine particles can be measured by, for example, an electrical sensing zone method. The concentration of fine particles may be, for example, not more than $10^{10}$ particles/mL.

The fine particles may either be inorganic fine particles or organic fine particles. The dispersion medium may be water or an organic dispersion medium. In view of handleability, the dispersion medium is preferably water.

The fine-particle-containing liquid may be a liquid derived from a living body, such as blood, saliva, nasal discharge, or urine. In a case where the fine-particle-containing liquid is such a liquid derived from a living body, for example, red blood cells, white blood cells, blood platelets, pollens, bacteria, viruses, and other cells can be considered the fine particles.

[2. Method of Increasing Concentration of Target Fine Particles]

A method of increasing the concentration of fine particles in accordance with an embodiment of the present invention includes: an introducing step including introducing a liquid containing fine particles into a main channel; a capturing step including allowing the liquid to drain into a side channel connected to a side face of the main channel and capturing target fine particles at a place where the side channel and the main channel are connected together; a releasing step including releasing the captured target fine particles into the main channel; and a concentrating step including allowing the target fine particles thus released to move into a chamber provided at an end of the main channel so that the target fine particles which have increased in concentration are stored in the chamber, wherein at least one of the height and width of the side channel is smaller than the particle size of the target fine particles. The method of increasing the concentration of target fine particles may be carried out with use of the foregoing channel device in accordance with an embodiment of the present invention.

The method of increasing the concentration of target fine particles makes it possible to increase the concentration of target fine particles which are contained in a slight amount in a liquid to high level. This makes it possible, for example, in a case where viruses are selected as the target fine particles, to increase the concentration of the viruses in a sample taken from a test subject. The method thus makes it easy to detect the viruses, and is also useful for early diagnosis of infectious diseases.

Figure 3:
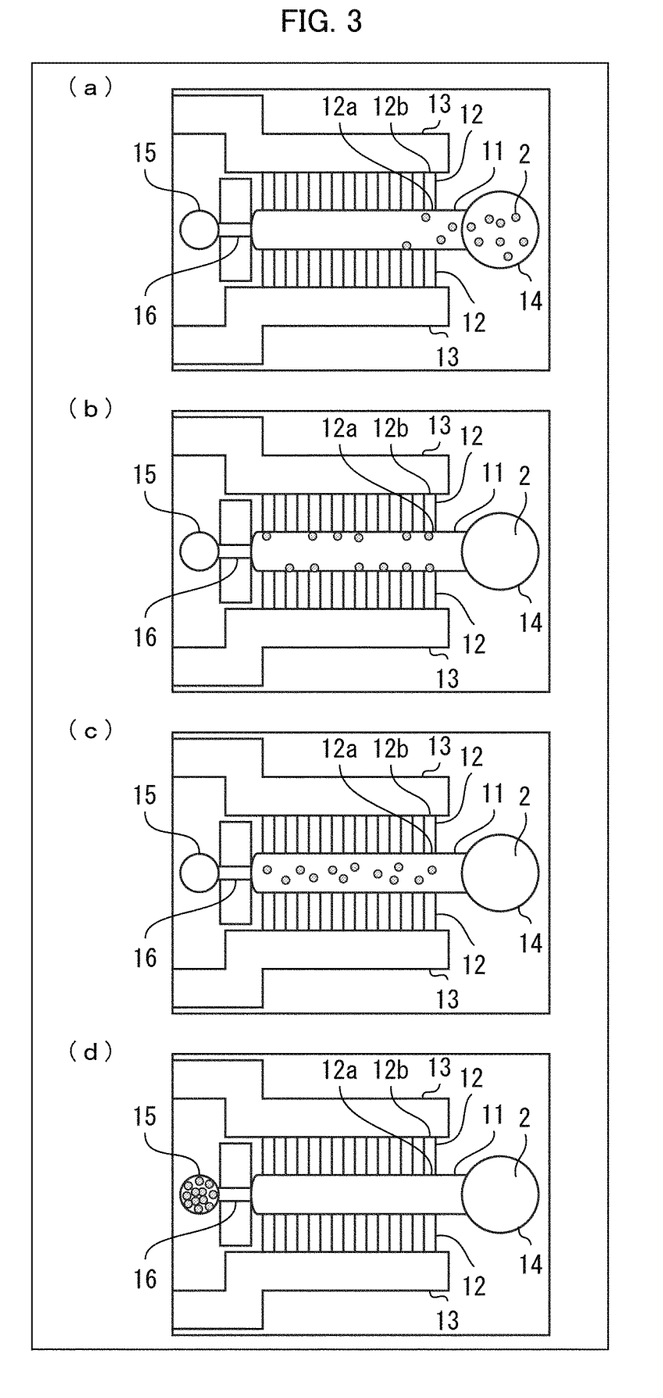
FIG. 3 schematically illustrates an overview of a method of increasing the concentration of fine particles in accordance with an embodiment of the present invention.

The following description will discuss the method of increasing the concentration of target fine particles with reference to FIG. 3. FIG. 3 schematically illustrates an overview of a method of increasing the concentration of target fine particles in accordance with an embodiment of the present invention.

<2-1. Introducing Step>

The method of increasing the concentration of target fine particles includes an introducing step that includes introducing a fine-particle-containing liquid into a main channel. In (a) of FIG. 3, a liquid that contains fine particles 2 is introduced into a liquid inlet part 14. The fine particles 2, together with the liquid, flow through the main channel 11.

<2-2. Capturing Step>

The method of increasing the concentration of target fine particles includes a capturing step that includes allowing the liquid to drain into a side channel(s) connected to a side face(s) of the main channel and capturing the target fine particles at a place(s) where the side channel(s) and the main channel are connected together. In the capturing step, target fine particles 2, which are carried by flows of a liquid draining toward the side channels 12, are captured at the first junctions 12a as illustrated in (b) of FIG. 3. This is because the particle size of the target fine particles 2 is greater than at least one of the height and width of each side channel 12 at the first junction 12a.

In doing so, when the pressure at the first junctions 12a is higher than the pressure at the second junctions 12b, the flow rate of the liquid flowing through the side channels 12 toward the liquid drainage channels 13 increases, and the time taken for the liquid to drain away can be shortened. Note that, in the capturing step, it is preferable that the entire liquid drains into the side channels 12.

<2-3. Releasing Step>

The method of increasing the concentration of target fine particles includes a releasing step that includes releasing the captured target fine particles to the main channel. In the releasing step, as illustrated in (c) of FIG. 3, the target fine particles 2, which have been captured at the first junctions 12a, are released into the main channel 11. The target fine particles 2 can be released by, for example, (1) releasing a pressure (which has been applied to the side channels 12 so as to make the pressure at the first junctions 12a higher and to accelerate liquid drainage), (2) applying a pressure to the side channels 12 so that the fluid pressure at the first junctions 12a is lower than the fluid pressure at the second junctions 12b, or (3) passing an additional liquid through the main channel 11.

<2-4. Concentrating Step>

The method of increasing the concentration of target fine particles includes a concentrating step that includes allowing the target fine particles thus released to move into a chamber provided at an end of the main channel so that the target fine particles which have increased in concentration are stored in the chamber. In the concentrating step, as illustrated in (d) of FIG. 3, the target fine particles 2, which have been released into the main channel 11, are allowed to move into the chamber 15 together with a small amount of liquid (e.g., liquid that has flowed back from the side channels 12 or the additional liquid introduced into the main channel 11). The target fine particles 2, which have moved to the chamber 15, have increased in concentration. In this specification, the phrase "increase the concentration of fine particles" is intended to mean increasing the number of fine particles per unit volume of a liquid relative to the number of fine particles per unit volume of a liquid at the time when the fine-particle-containing liquid was introduced. The channel device 1 is capable of increasing the concentration of fine particles usually 100 times or more, preferably 500 times or more, more preferably 1000 times or more.

It is preferable that a liquid flow preventer part (such as a water-repellent channel 16) is provided between the main channel 11 and the chamber 15 and that a liquid pressure difference is capable of being caused such that the pressure at the end of the main channel 11 at which a liquid is introduced is higher, because this makes it possible to carry out the concentrating step anytime desired.

[3. Method of Producing Channel Device]

The following description will discuss a method of producing a channel device in accordance with an embodiment of the present invention. A channel device in accordance with an embodiment of the present invention may be produced by: preparing a member that has microchannels in the usual manner; and optionally connecting the member with a fluid pressure controller, a sensor, and/or the like.

The method of producing a channel device can be selected appropriately according to a material for the channel device. The material for the channel device may be: a silicone resin such as polydimethylsiloxane; a poly(methyl methacrylate) resin; an olefin-based resin such as cyclic olefin copolymer; or glass or the like. The method of producing a channel device is not particularly limited, and may be achieved by soft lithography, nanoimprint, or thin film lamination. The following description discusses an example in which the method includes soft lithography of a silicone resin, with reference to FIG. 4.

First, a mold for channels is prepared in the following manner. A photoresist is applied to a substrate 21 made of an appropriate material (e.g., silicone), and thereby a resist film is formed. Channel patterns are formed by exposure to light. The channel patterns may be formed in the following manner: a pattern 22 corresponding to side channels (see (a) of FIG. 4) is formed; and then a pattern 23 corresponding to a main channel is formed (see (b) of FIG. 4). A difference in height at each first junction can be created by forming resist films different in thickness.

Next, a silicone resin is poured onto the mold prepared in the above step. The silicone resin is cured by heat, and then a member 24 that has the channel patterns imprinted therein is obtained (see (c) of FIG. 4). A surface, which makes contact with a liquid, of the member 24 may optionally be made hydrophilic. The surface can be made hydrophilic by, for example, forming a hydrophilic film by pulsed plasma CVD, carrying out surface treatment by an oxygen plasma method, or modifying the surface with vacuum-ultraviolet light.

Figure 4:
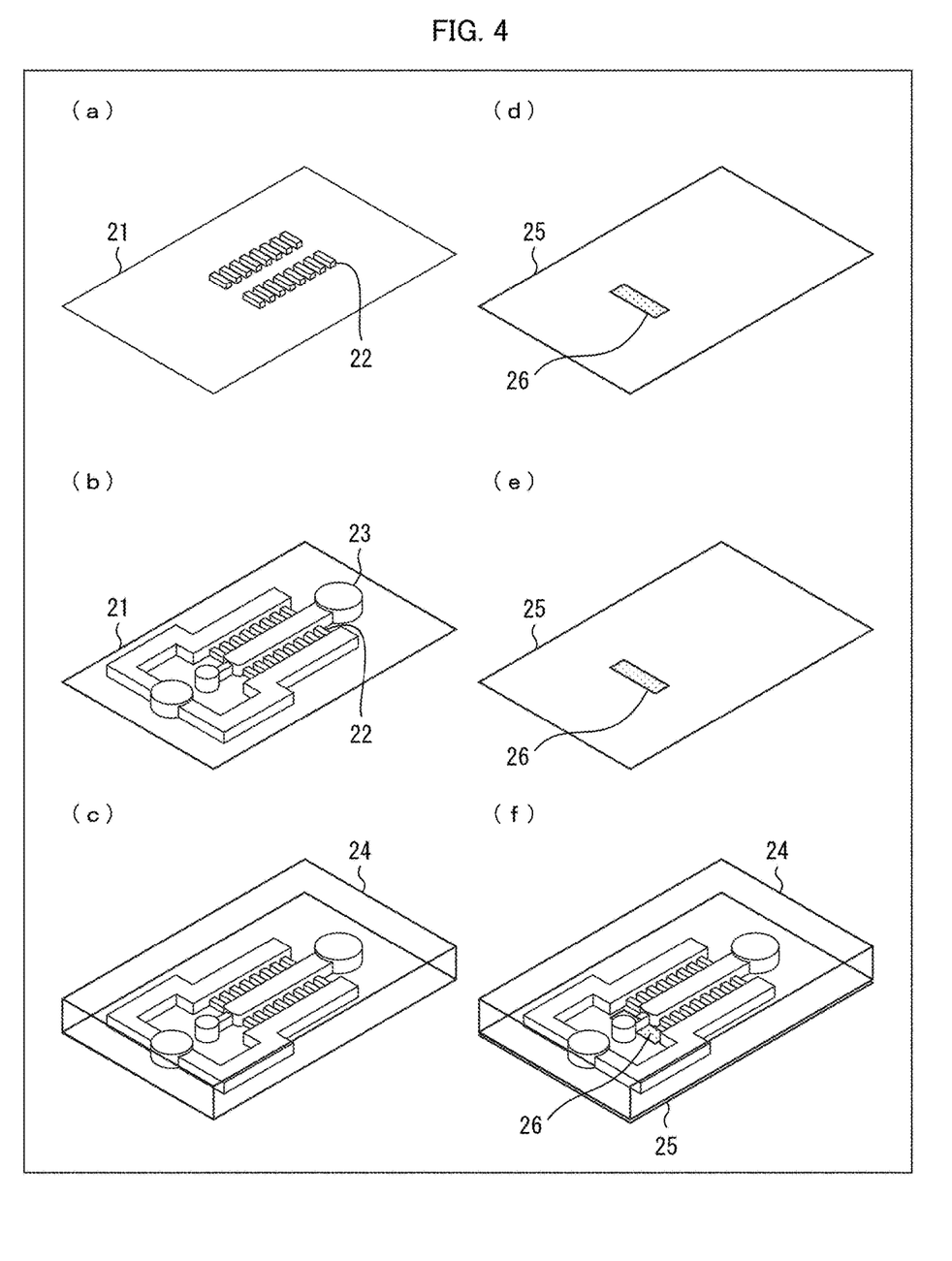
FIG. 4 schematically illustrates a method of producing a channel device in accordance with an embodiment of the present invention.

On the other hand, a substrate 25 corresponding to the bases of the channels is prepared (see (d) of FIG. 4). A surface of the substrate 25 may be made hydrophilic and/or made water-repellent. A water-repellent region 26 may be formed on the substrate 25 (see (d) of FIG. 4) and then the surface of the substrate 25 except for the water-repellent region 26 may be made hydrophilic (see (e) of FIG. 4). The surface can be made hydrophilic by, for example, forming a hydrophilic film by pulsed plasma CVD, carrying out surface treatment by an oxygen plasma method, or modifying the surface with vacuum-ultraviolet light. The surface can be made water-repellent by, for example, forming a water-repellent film by pulsed plasma CVD or treating the surface with a fluorine gas.

Lastly, the member 24 and the substrate 25 are bonded together (see (f) of FIG. 4).

The matters discussed in the foregoing sections can also apply to other sections as appropriate. The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following description will discuss the present invention in more detail based on Examples. Note, however, that the present invention is not limited to the following Examples.

Production Example: Preparation of Channel Device

First, a negative photosensitive resist (SU-8 2000.5, available from MicroChem) was applied onto a silicon substrate 100 mm in diameter (4-in. silicon wafer, available from ELECTRONICS AND MATERIALS CORPORATION) to form a resist film 0.5 µm in thickness. Next, with the use of a maskless exposure apparatus (high-luminance LED lithography apparatus, available from PMT Corporation.), a pattern of side channels was formed by LED lithography. Each side channel was 5 µm in width, 0.5 µm in height, and 50 µm in length. The number of side channels was 660. The side channels were spaced apart from each other by 15 µm.

Note here that, because openings of the side channels at first junctions each have a size of 5 µm×0.5 µm, fine particles greater than this size cannot pass through the side channels. Specifically, fine particles having a particle size greater than the height (0.5 µm) of the side channels cannot pass through the side channels.

Next, a negative photosensitive resist (SU-8 3050, available from MicroChem) was applied onto the silicon substrate to form a resist film 30 µm in thickness. Next, with use of an exposure apparatus (mask aligner) (PEM-800, available from Union Optical Co., LTD.), a pattern of a main channel, liquid drainage channels, liquid inlet part and chamber was formed. The main channel was 200 µm in width, 30 µm in height, and 6 mm in length. Each liquid drainage channel was 100 µm in width and 30 µm in channel height.

Polydimethylsiloxane (Sylgard 184 (registered trademark) Silicone Elastomer, available from Dow Corning Toray Co., Ltd.) was poured onto the mold having channel patterns prepared in the foregoing steps, and was cured by heat. Then, a channel structure made of polydimethylsiloxane, having the channel patterns imprinted therein, was released from the mold.

A surface, which will face a silica glass substrate (described later), of the channel structure was subjected to an oxygen plasma treatment with use of a plasma cleaner (FEMTO CUTE-MP, available from Femto Science Inc). In this way, the surface of the channel structure was made hydrophilic.

On the other hand, a water-repellent film made of $SiC_x$ was formed by pulsed plasma CVD in a region, which corresponds to a water repellent channel, of a surface of a silica glass substrate (4-in. synthetic silica glass wafer, available from DAICO MFG CO., Ltd.). The water-repellent film was formed with use of a pulsed plasma CVD apparatus (for laboratory use, available from SHINKO SEIKI CO., LTD.).

Next, a hydrophilic film made of $SiO_x$ was formed by pulsed plasma CVD in a region, which excludes the water-repellent film, of the surface of the silica glass substrate. The hydrophilic film was formed with use of the pulsed plasma CVD apparatus (for laboratory use, available from SHINKO SEIKI CO., LTD.).

The obtained channel structure, which had been made hydrophilic, and the obtained silica glass substrate were bonded together.

A hole 4 mm in diameter was made in a liquid inlet part, and the liquid inlet part was connected to a fluid pressure controller (ELVEFLOW OB1, available from Elvesys) in a concentrating step. Also, a hole 2 mm in diameter was made in part of each liquid drainage channel, and the liquid drainage channel was connected to the fluid pressure controller (ELVEFLOW OB1, available from Elvesys).

Example 1: Increasing the Concentration of Carboxy-Modified Polystyrene Fine Particles Example 1-1

First, a dispersion liquid containing carboxy-modified polystyrene fine particles having a particle size of 6 µm (Polybead (registered trademark) Carboxylate Microspheres 6.00 µm, available from Polysciences) was used. The dispersion liquid was diluted with a phosphate buffer, and thereby a dispersion liquid having a fine particle concentration of $10^4$ particles/mL (liquid volume: 30 µL) was prepared. This dispersion liquid was allowed to flow through the channel device prepared in the foregoing Production Example, and thereby the fine particles were increased in concentration.

Figure 5:
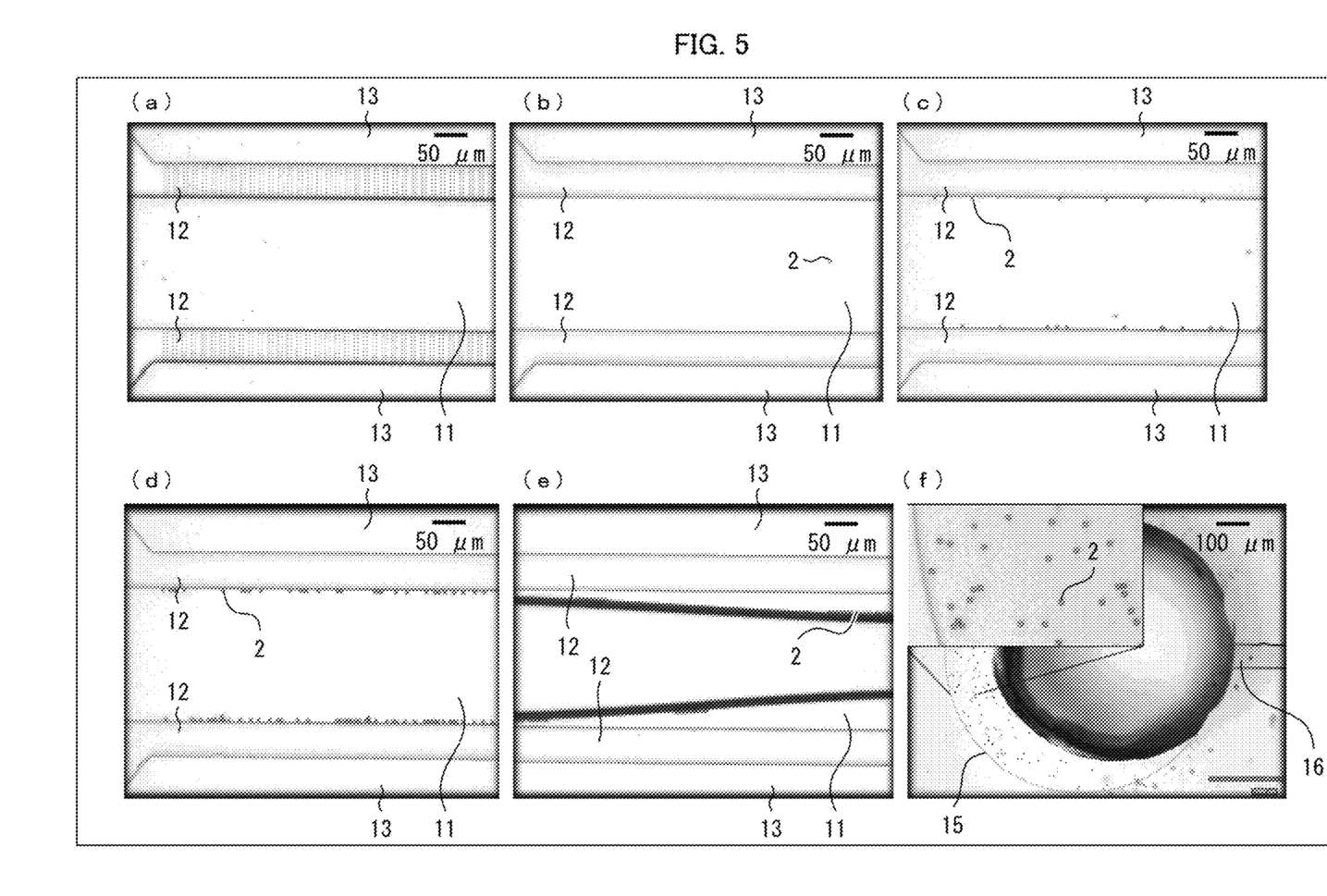
FIG. 5 shows how fine particles are increased in concentration in Example 1-1, observed under a digital microscope.

FIG. 5 shows how fine particles are increased in concentration, observed under a digital microscope (KH-8700, available from HIROX CO., LTD.). (a) of FIG. 5 shows the channel device before the dispersion liquid is introduced. The dispersion liquid prepared in the foregoing manner was dropped into the liquid inlet part, and was allowed to flow through the channels. Note that, in (b) to (e) of FIG. 5, each single side channel 12 is not clearly defined, due to the refractive index effect caused by a liquid flowing through the side channels 12. (b) of FIG. 5 shows fine particles 2 flowing through the main channel 11. In such circumstances, a pressure of −80 kPa was applied with use of the fluid pressure controller so that the fluid pressure on the main channel side would be higher than the fluid pressure on the liquid drainage channel side. (c) of FIG. 5 shows how fine particles 2 are captured at the openings of the side channels 12. As a result, drainage of a liquid took about 10 minutes to complete. As shown in (d) of FIG. 5, the fine particles 2 were captured at the openings of the side channels 12.

At the point in time in which the drainage of the liquid completed, the application of the pressure was stopped. As a result, the carboxy-modified polystyrene fine particles 2, which could not pass through the openings of the side channels 12 and were captured, were released into the main channel 11 as shown in (e) of FIG. 5.

Next, a pressure of 10 kPa was applied with use of the fluid pressure controller so that the fluid pressure on the liquid inlet part side is higher than the fluid pressure on the chamber side. As a result, the carboxy-modified polystyrene fine particles 2, together with a slight amount of a liquid, passed through the water-repellent channel 16 and moved to the chamber 15 (see (f) of FIG. 5).

(Results)

The concentration of the carboxy-modified polystyrene fine particles, which had moved to the chamber, was about $10^7$ particles/mL. This result showed that the concentration of fine particles was increased about 800 times.

Example 1-2

The same operations as described in the foregoing Production Example were carried out, except that the length of each side channel was changed to 100 μm. In this way, a channel device was prepared. The same test as described in Example 1-1 was carried out using carboxy-modified polystyrene fine particles having a particle size of 1 μm.

Specifically, 30 μL of a dispersion liquid containing carboxy-modified polystyrene fine particles at a fine particle concentration of $4.55\times10^4$ particles/mL was dropped into the liquid inlet part. A pressure of −80 kPa was applied with use of the fluid pressure controller so that the fluid pressure on the main channel side would be higher than the fluid pressure on the liquid drainage channel side. As a result, drainage of a liquid took about 33 minutes to complete.

(Results)

Figure 6:
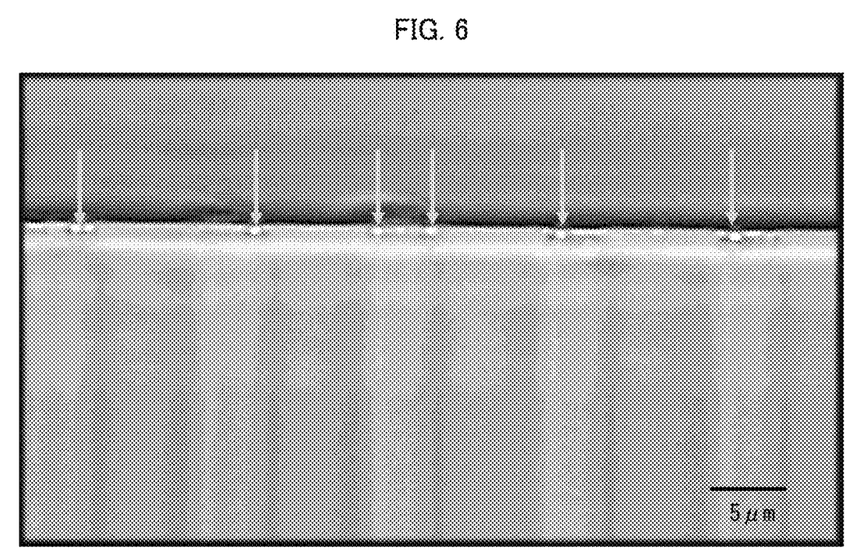
FIG. 6 shows fine particles captured in Example 1-2, observed under a digital microscope.

FIG. 6 shows captured fine particles observed under the digital microscope (KH-8700, available from HIROX CO., LTD.). The arrows in FIG. 6 indicate the captured carboxy-modified polystyrene fine particles.

The concentration of the carboxy-modified polystyrene fine particles, which had moved to the chamber, was about $10^7$ particles/mL. This result showed that the concentration of fine particles was increased about 800 times.

Example 2: Separation of *Escherichia Coli*

The same operations as described in the foregoing Production Example were carried out, except that the length of each side channel was changed to 100 μm. In this way, a channel device was prepared. With use of the channel device, *Escherichia coli* cells (in the shape of columns about 1 μm×5 μm in size) were captured from a phosphate buffer containing the *Escherichia coli* cells.

Specifically, 30 μL of a phosphate buffer containing *Escherichia coli* cells was dropped into the liquid inlet part. A pressure of −80 kPa was applied with use of the fluid pressure controller so that the fluid pressure on the main channel side would be higher than the fluid pressure on the liquid drainage channel side. As a result, drainage of a liquid took about 30 minutes to complete.

(Results)

Figure 7:
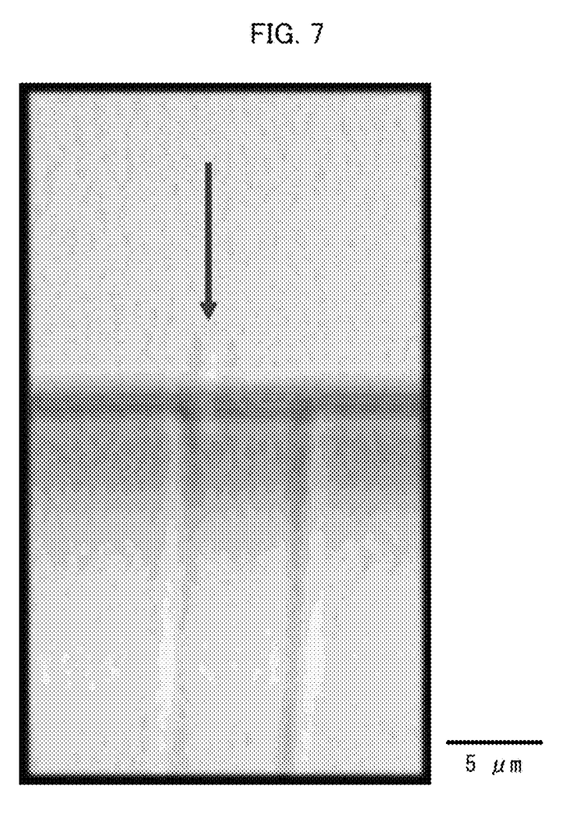
FIG. 7 shows an *Escherichia coli* cell captured in Example 2, observed under a digital microscope.

FIG. 7 shows a captured *Escherichia coli* cell observed under the digital microscope (KH-8700, available from HIROX CO., LTD.). The arrow in FIG. 7 indicates the captured *Escherichia coli* cell. In this way, a channel device in accordance with an embodiment of the present invention is also capable of capturing relatively soft fine particles such as *Escherichia coli* (cells).

INDUSTRIAL APPLICABILITY

The present invention can be used in technical fields in which, for example, detection of a slight amount of fine particles is useful (e.g., early diagnosis of infectious diseases).

REFERENCE SIGNS LIST 1 channel device
2 fine particle
11 main channel
12 side channel
13 liquid drainage channel
15 chamber
16 water-repellent channel (liquid flow preventer part)

The invention claimed is:

1. A channel device comprising:
    a main channel configured to allow a liquid containing fine particles to flow therethrough;
    a chamber that is provided at an end of the main channel and that is configured to store target fine particles which have increased in concentration;
    side channels that are configured to allow unwanted liquid to drain therethrough, the side channels each having opposite first and second ends, the first ends of the side channels being connected to opposite side faces of the main channel,
    a fluid pressure controller configured to be capable of applying a fluid pressure to the side channels so that a pressure at the first ends is lower than a pressure at the second ends, wherein
    at least one of a height and a width of each of the side channels is smaller than a particle size of the target fine particles, and
    a liquid flow preventer part is provided between the main channel and the chamber.

2. The channel device as set forth in claim 1, wherein each of the side channels has the second end connected to a liquid drainage channel, the liquid drainage channel having a width that is equal to or greater than the width of each of the side channels and having a height that is equal to or greater than the height of each of the side channels.

3. The channel device as set forth in claim 1, comprising a plurality of the side channels.

4. A method of increasing a concentration of target fine particles, the method comprising:
    an introducing step comprising introducing a liquid containing fine particles into a main channel;
    a capturing step comprising (i) allowing the liquid to drain into side channels, the side channels each having opposite first and second ends, the first ends of the side channels being connected to opposite side faces of the main channel, and (ii) capturing target fine particles at places where the side channels and the main channel are connected together;
    a releasing step comprising releasing, into the main channel, the target fine particles thus captured; and a concentrating step comprising allowing the target fine particles thus released to move into a chamber provided at an end of the main channel so that the target fine particles which have increased in concentration are stored in the chamber, wherein at least one of a height and a width of each of the side channels is smaller than a particle size of the target fine particles, a liquid flow preventer part is provided between the main channel and the chamber, and the side channels undergo the following (i) or (ii):
  (i) in the capturing step, application of fluid pressure is carried out so that a pressure at the first ends of the side channels is higher than a pressure at the second ends of the side channels, and, in the releasing step, the application of fluid pressure is stopped or another application of fluid pressure is carried out so that the pressure at the first ends of the side channels is lower than the pressure at the second ends of the side channels; or
  (ii) in the releasing step, application of fluid pressure is carried out so that the pressure at the first ends of the side channels is lower than the pressure at the second ends of the side channels.

5. The method as set forth in claim 4, wherein each of the side channels has the second end connected to a liquid drainage channel, the liquid drainage channel having a width that is equal to or greater than the width of each of the side channels and having a height that is equal to or greater than the height of each of the side channels.

6. The method as set forth in claim 4, wherein a plurality of the side channels are provided.

* * * * *